US008419914B2

(12) United States Patent
Stoica et al.

(10) Patent No.: US 8,419,914 B2
(45) Date of Patent: Apr. 16, 2013

(54) POTENTIOMETRIC SENSORS BASED ON ANIONIC BORON CLUSTERS

(75) Inventors: Anca Lulia Stoica, Barcelona (ES); Clara Viñas, Barcelona (ES); Francesc Teixidor, Barcelona (ES)

(73) Assignee: Consejo Superior de Investigaciones Científicas (ES)

( * ) Notice: Subject to any disclaimer, the term of this patent is extended or adjusted under 35 U.S.C. 154(b) by 15 days.

(21) Appl. No.: 13/063,752

(22) PCT Filed: Sep. 10, 2009

(86) PCT No.: PCT/ES2009/070377
§ 371 (c)(1),
(2), (4) Date: Jun. 22, 2011

(87) PCT Pub. No.: WO2010/029207
PCT Pub. Date: Mar. 18, 2010

(65) Prior Publication Data
US 2011/0247945 A1    Oct. 13, 2011

(30) Foreign Application Priority Data
Sep. 12, 2008    (ES) .................................. 200802603

(51) Int. Cl.
*G01N 27/333*    (2006.01)
(52) U.S. Cl.
USPC .......................................... 204/416; 205/789
(58) Field of Classification Search .......... 204/416–418; 205/778.5, 779, 789, 792
See application file for complete search history.

(56) References Cited

U.S. PATENT DOCUMENTS

| 5,985,117 | A | 11/1999 | Bachas |
| 6,423,199 | B1 * | 7/2002 | Tinker et al. ................. 204/536 |
| 2005/0023153 | A1 | 2/2005 | Bakker |

FOREIGN PATENT DOCUMENTS

| EP | 0551769 | * | 7/1993 |

OTHER PUBLICATIONS

Bobacka et al., "Influence of anionic additive on Hg2+ interference on Ag+-ISEs based on [2.2.2]p,p,p-cyclophane as neutral carrier," Talanta. 63, 2004, pp. 135-138.
Peper et al., "Ion-pairing ability, chemical stability, and selectivity behavior of halogenated dodecacarborane cation exchangers in neutral carrier-based ion-selective electrodes," Anal. Chem., 75, 2003, pp. 2131-2139.
Stoica et al., "Gobaltabisdicarbollide anion receptor for enantiomer-selective membrane electrodes," Chem. Commun., 2009, pp. 4988-4990.
Stoica et al., "Application of the cobaltabisdioarbollide anion to the development of ion selective PVC membrane electrodes for tuberculosis drug analysis," Chem. Commun., 2008, pp. 6492-6494.
International Search Report issued in International application No. PCT/ES2009/070377, mailed Dec. 18, 2009.
Written Opinion of the international Searching Authority issued in International application No. PCT/ES2009/070377, mailed Dec. 18, 2009.
International Preliminary Report on Patentability issued in International application No. PCT/ES2009/070377, issued on Mar. 15, 2011.

* cited by examiner

*Primary Examiner* — J. Christopher Ball
(74) *Attorney, Agent, or Firm* — Byrne Poh LLP; Nina R. Horan

(57) ABSTRACT

Potentiometric sensor comprising an ion selective electrode and the latter, on its part, containing a membrane characterized in that it comprises: a thermoplastic material; an electroactive substance based on a salt wherein the cation is the protonated form of the analyte to be determined and the anion is a cluster which comprises boron atoms; and a plasticizing agent. In addition, the invention further relates to the use of said sensor for the detection and/or quantification of a compound containing at least one nitrogen atom.

16 Claims, No Drawings

POTENTIOMETRIC SENSORS BASED ON ANIONIC BORON CLUSTERS

CROSS-REFERENCE TO RELATED APPLICATION

This application is a national stage application under 35 U.S.C. 371 of the International Application No. PCT/ES2009/070377, filed Sep. 10, 2009, which claims priority to Spanish Patent Application No. P200802603, filed Sep. 12, 2008, both of which are hereby incorporated by reference in their entireties.

The present invention relates to a potentiometric device comprising a sensor membrane based on anionic boron clusters; hence the invention belongs to the scientific and technological field of chemistry, namely to the chemical analysis of compounds, which contain protonable nitrogen as an integral element or can be quarternised, as well as in applications in sectors such as chemistry and/or pharmaceutics.

STATE OF THE ART

Currently, there are various analytical methods, which are used for determination of analytes with nitrogen (such as antibiotics, amino acids, peptides, dyes, etc.) in various types of matrices[1-10], in particular chromatographics, spectrophotometrics, voltamperometrics and amperometrics. These methods are very efficient, but, in general, they are slow and relatively expensive for performing a routine analysis. In addition, these drawbacks are aggravated in the case of analyses performed outside of the laboratory. Due to the growing demand for analyses in the pharmaceutical industry (for example, quality control, drug monitoring, etc.), the availability of fast analytical processes is becoming a necessity. Conventional methods are based on chromatographic analysis (TLC; HPLC-UV, GC-MS)[11-13]. These methods require complex preliminary treatments and much dedication which makes them unsuitable for analysing a large number of samples.

On the other hand, the analytical methods, which are mostly used for determining the content of amino acids in biological media and in food samples, are volumetry, capillary electrophoresis, voltamperometry, chemiluminescence, amperometry, polarography, chromatography coupled with various detection systems (such as ultraviolet-visible absorption, fluorescence, and mass spectrometry), fluorescence spectroscopy and spectrophotometric methods[14-19]. Among these methods, volumetry is simple, but it is neither sensitive nor selective; capillary electrophoresis is a method with high resolution, but it is not easy to perform because it needs a highly specialised person. Voltamperometric methods are a selective, sensitive and relatively inexpensive technique, but in many cases it is difficult to obtain maximum information. Some methods require sophisticated preliminary treatment of the samples, longer time for performing the analysis, very expensive equipment, and specialization of the person. For this reason, it is important to develop more direct and faster techniques for the analysis of compounds, in general, and those that contain nitrogen, in particular.

Some of these electrochemical methods (polarography[20], voltamperometry[21]) are already used with good results in the analysis of compounds with electroactive nitrogen. For these applications, working electrodes such as carbon, gold or platinum are used. In order to improve the selectivity of the electrochemical signal, chemically modified electrodes can be used. In recent years, the importance of electrochemical detection as a sensitive and selective technique for electroactive compounds has increased. Screen-printing electrodes represent one of the most interesting alternatives in the design of electrochemical sensors[22]. These electrodes have found wide application as sensors for biomedical, environmental and industrial analyses[23].

On the other hand, potentiometry (and, more specifically, ion selective electrodes (ISEs)) is a very economic and efficient analytical method for the determination of many analytes[28-29].

In particular, potentiometric sensors based on ion pairs on the basis of methylene blue-silicotungstate have been used with success for determination of certain dyes such as the methylene blue[24].

Various types of ISEs based on biospecific molecules, ion exchange or neutral carriers have also been used for the analysis of pharmaceutical compounds[25-26].

The method using a PVC membrane is the most simple, most inexpensive and most direct type of ISE. The advances in pharmaceutical analysis with ISEs have permitted the direct and selective measurement of the activity of various organic cations or anions of interest for the pharmacology, in the majority of the cases without preliminary treatment of the active substance of the matrix of the formulation. The only operation the sample needs is to be dissolved in water. Thus, pharmaceutical compounds (novocaine, dimedrol, lidocaine, papaverine) have already been determined by using ISEs based on PVC membranes, which use tetraphenylborate as a generator of the ion pair[27].

The ion selective electrodes can be miniaturised, so that they could be used in analyses in vivo or in vitro, for analyses of flows in the industry or in the sampling points. It is known from bibliographic data that precision and accuracy in the analysis of antibiotics for commercial preparations are generally better when using PVC membrane sensors rather than in the case of using liquid membranes[30].

A study related to the ion selective electrodes for the determination of ammonium organic ions has shown that the habitual components of the membrane are: plasticizers NPOE, DBP, DNA dinonyl adipate, TEHP tris(2-ethylhexyl) phosphate and potassium tris(nonyloxy)benzenesulfonate (K(TNOBS); as ion exchangers, potassium tetrakis(4-clorophenyl)borate (K(TpCIPB)), and dibenzo-18-corona-6 as a neutral cationic carrier; and tetradecylammonium (TDA) $NO_3$ nitrate as a cationic additive[31].

Ion selective electrodes are easy to manufacture and convenient for operation; that is why this method has some advantages compared to the other techniques; the preparation of the membrane is simple, the electroactive components are easy to prepare, and the tools are very accessible, cheaper and easier to operate than those necessary for the HPLC, FIA, spectrophotometry. However, these above-described membranes are less stable compared to the ions that are generally used, such as the case of the tetraphenylborate.

DESCRIPTION OF THE INVENTION

In order to determine the existence of a given chemical compound and its concentration of biological fluids, natural or synthetic fluids, analytical tools based on physical methods, chemical methods or a combination thereof are necessary. The existing analytical tools are very varied, and practically every compound can be detected directly or indirectly; the problem is in the complexity of the technique, the cost of the necessary equipment, the required training for the analyst, the time that is necessary for completing the detection and quantification of the sought analyte or the possibility for the equipment to be mobile or stationary. Portable and light equipment are important and can be even more important for the continuous control of a specific analyte and for its controlled dispensing, for example, in the case of a drug, or for its availability under any situation and circumstance.

Generally, large apparatuses have sufficient options, which do are not required to be selective to a specific analyte; on the contrary, the small devices must be selective to one or a few analytes in order to be of technological interest. On the other hand, large apparatuses are stationary and expensive, while the small ones offer the possibility to be mobile at a low cost. The latter ones need a sensor element that is capable of selectively detecting a given analyte and its concentration and a transducer that is capable of transmitting the signal, no matter what its type is, e.g. acoustic, optical or electric, and which must be proportional to the concentration of the electrolyte.

Therefore, the key point for a mobile chemical sensor is its selectivity, i.e. its ability to respond mainly to one unique analyte, and that the signal has to be proportional to its concentration.

In this way, the present invention provides a membrane that can be coupled to different transducers in order to detect analytes which are chemically related to the cation present in the membrane. Basically, the resulting sensor devices are composed of a sensor membrane incorporating a salt of an anion that is a cluster, which contains boron among other elements such as, for example, borane, carborane or metallocarborane, mono- or poly-anionic, with a cationic form of the analyte that has to be measured, along with a plasticizer, a polymer and other optional additives. More specifically, these sensors make it possible to detect and quantify a given analyte containing one or more nitrogen atoms in its molecule.

There are other advantages which make potentiometry an alternative for the analysis of compounds with nitrogen compared to the other methods that are used currently:

Ion selective electrodes (ISEs) are easy to manufacture and convenient to operate. The method has certain advantages compared to the other techniques used in the state of the art; the preparation of the membrane is simple, the electroactive components are easy to prepare, and the tools are very accessible, cheaper and easier to operate than those required for HPLC, FIA or spectrophotometry.

The potentiometric determination can be performed in several minutes, in contrast to the longer times that are necessary for analysis with other official or traditional standard methods.

The present invention discloses the design and the general functional characteristics of a potentiometric sensor with a plastic membrane for nitrogen compounds. Some of the analytes to be determined may be antibiotics for the treatment of tuberculosis, such as isoniazid or the pyrazinamide. The ease was demonstrated for converting an interference, for example, pyrazinamide is an interference for the isoniazid ISE, in the main ion of another ISE. In other words, the main ion in a second electrode is pyrazinamide, while isoniazid is the interferential ion. Both electrodes are practically identical and are based on the cobalt bis(dicarbollide) anion. The electrodes in the present invention have good analytic characteristics for determination of the analyte without the need for any preliminary separation and show a good reproducibility.

The ISE membrane not only acts as a polymeric matrix for controlled release of the reagent, as this takes place in the polymeric release systems for the optical sensors, but it acts also as a transducer for selective potentiometric detection. This combination makes ISE very attractive for the miniaturisation of the sensor.

In the ISEs, the composition of the membrane is the most important part of this "device". Simply by changing the electroactive part (or the electroactive substance) of the membrane it is possible to have another electrode that is selective to another analyte, which makes it possible to determine it from a complex matrix, such as pharmaceutical, clinical or environmental samples.

A distinctive feature of the membrane in the present invention with respect to the ions that are generally used, such as the tetraphenylborate, is that the anions of the ion pair in this invention are capable of self-organizing themselves by means of dihydrogen bonds $C_c$—H . . . H—B, (metallocarboranes) and to be non-covalently bonded to the plasticizer by means of hydrogen bonds $C_c$—H . . . O, (metallocarboranes), or to be able to have weak dihydrogen bonds B—H . . . H—N with the electroactive cation. All of this implies greater stability of the structure by fixing the anions and providing them with a more limited mobility. This produces better sensor membranes and a capacity to detect very similar compounds such as enantiomers.

Therefore, a first aspect of the present invention comprises a membrane for a potentiometric sensor characterized in that it comprises (hereinafter the membrane of the invention) the following:

A thermoplastic material
An electroactive substance; and
A plasticizing agent.

The electroactive substance of the membrane of the invention is a salt of the type $[\text{cation}]_x[\text{anion}]_y$, wherein:

The cation is a protonated form of the analyte to be determined or it is the same analyte, if it is already there, in normal conditions, in cationic form. This cation can have one, two or more positive charges depending on the concentration of the acid during the protonation and the number of protonable nitrogens that the analyte has or which have a positive charge in normal conditions The anion of the salt is a cluster containing boron atoms among other elements.

In the present invention, "cluster containing boron atoms" means a compound of polyhedric form whose vertices are occupied by boron atoms. These clusters can be, without limitation, borane, carborane or metallocarborane with one, two or more negative charges.

A preferred embodiment of the membrane of the invention comprises salt wherein the borane has the formula $(B_nX_mH_{n-m})^{2-}$ or $(LB_nH_n)^-$, where:

n has a value between 6 and 12,
X is selected from a list that contains hydrogen (H), halogen, alkyl group or aryl group,
m has a value between 0 and 12,
L is a XR'R"R''' or XR'R" group, where X is a nitrogen (N) atom, phosphorus (P) atom, sulfur (S) atom or oxygen (O) atom, and R', R" and R''' are radicals, equal or different, selected among one atom of H, one alkyl group or one aryl group.

When m is equal to 0, i.e. X does not exist, the formula would be $(B_nH_n)^{2-}$. Examples of this type of anions can be, but are not limited to, $(B_{10}H_{10})^{2-}$ or $(B_{12}H_{12})^{2-}$.

Another preferred embodiment of the membrane of the invention comprises salt wherein the anion is carborane and has the formula $(RCB_nX_mH_{n-m})^-$, where:

R is H, an alkyl group or an aryl group,
n has a value between 5 and 11,
X is a halogen, an alkyl group or an aryl group, and
m has a value between 0 and 11.

When m is equal to 0, i.e. X does not exist and the formula would be $(RCB_nH_n)^-$. Examples of this type of anions can be, but are not limited to, $(CB_{11}H_{12})^-$ or $(CB_9H_{10})^-$ Another preferred embodiment of the membrane of the invention comprises salt wherein the anion is metallocarborane and has the formula $[M(C_2B_9H_{11})_2]^-$, $[M(C_2B_9H_{11})_2]^{2-}$, any of their derivatives, such as, for example, but not limited to, $[M(C_2B_9H_{11-y}X_y)_2]^-$ (where X=hydrogen, halogen, an alkyl group or an aryl group) or any combination, mono- or di-ionic, of at least two metallocarboranes, where M is a trivalent or divalent metal. Examples of this type of anions can be, but are not limited to, $[Co(C_2B_9H_{11})_2]^-$, $[Co(C_2B_9H_8Cl_3)_2]^-$, $[Co(C_2B_9H_8Br_3)_2]^-$ or $[Co(C_2B_9H_8I_3)_2]^-$.

"Alkyl" in the present invention means aliphatic, linear or branched chains with one or more carbon atoms, preferably between 1 to 20, more preferably between 1 and 10. Such as, for example, but not limited to, methyl, ethyl, n-propyl, i-propyl, n-butyl, t-butyl, n-pentyl, etc.

"Aryl" in the present invention has one aromatic carbocyclic chain with 6 or more carbon atoms, preferably from 6 to 12 carbon atoms; it can be with a single ring or with multiple rings, separated and/or condensed. Typical aryl groups contain from 1 to 3 rings, separated or condensed, and from 6 to approximately 18 carbon atoms with a ring, such as phenyl, naphthyl, indenyl, phenanthryl or anthracyl radicals.

In another preferred embodiment of the membrane of the invention, the thermoplastic material is polyvinylchloride (PVC) or other plastics with the same characteristics, such as, for example, but not limited to, polyethylene (PE), polypropylene (PP), polystyrene (PS), methacrylate (PMMA), vinyl polychloride (PVC), polyethylene terephthalate (PET), teflon (or polytetrafluorethylene, PTFE) or nylon (a type of polyamide). More preferably, the thermoplastic material is PVC.

In another preferred embodiment of the membrane of the invention, the plasticizing agent can be a polycarboxylic acid or any of its salts or its derived esters, such as, for example, but not limited to, phthalic acid, butyl benzyl phthalate (Bps), dibutyl phthalate (DBP), diethylhexyl phthalate (DEHP), diisononyl phthalate (DINP), dioctyl phthalate (DOP), adipic acid, bis(2-ethylhexyl)adipate (DEHA), dimethyl adipate (DMAD), monomethyl adipate (MMAD), dioctyl adipate (DOA), sebacic acid derivatives, such as dibutyl sebacate (DBS), bis(2-ethylhexyl sebacate) DOS; maleic acid derivatives, such as dibutyl maleate (DBM) or diisobutyl maleate (DIBM). Other plasticizing agents can be benzoate, vegetable oil, sulfonamide (BBSA-NBBS), organophosphate, such as, for example, but not limited to, tricresyl phosphate (TCP) or tributyl phosphate (TBP), polyether derived from glycol or polymeric plasticizers derived from nitrobenzene, such as, for example, but not limited to, nitrophenyl octyl ether (NPOE), nitrophenyl hexyl ether (NPHE), carbon disulfide or β-naphthyl salicylate.

In addition, other additives can be incorporated into the membrane of the invention.

The membrane of the invention can be deposited on a conductive, semi-conductive or non-conductive surface of the transducer. In the special case of an ISE, this membrane is deposited on a conductor or semiconductor, such as graphite or graphite compacted with binding material, or on an organic polymeric conductor in order to produce a potentiometric electrode. It will detect an analyte which is chemically related to the cation present in the salt.

Therefore, a second aspect of the present invention relates to an ion selective electrode (ISE), characterized in that it comprises the membrane of the invention on a support in the form of an electrical conductor or semiconductor which, preferably, can be graphite, any combination with graphite, or an organic polymer (hereinafter referred to as the ISE of the invention).

Another aspect of the present invention relates to a potentiometric sensor, characterized in that it comprises the ion selective electrode of the invention and a transducer. A transducer which can be electric, electronic, electromechanical, electromagnetic, photonic, or photovoltaic.

The process of obtaining the membrane of the invention comprises the preparation of the salt that is obtained by precipitating a cation of the analyte to be measured in water or another solvent, for example amino acid (A) protonate $[H_xA]^{x+}$, with an anion consisting of a cluster, which contains at least boron atoms, for example $[Co(C_2B_9H_{11})_2]^-$, producing salt with a composition of the type $[cation]_x[anion]_y$.

The resulting precipitate is mixed with PVC or other thermoplastic material and plasticizing agent such as dioctyl phthalate or another one described above.

Once the membrane of the invention has been obtained, it is dissolved in a solvent, such as, for example, but not limited to, THF (tetrahydrofuran), and is deposited on a conductor or semiconductor, for example, but not limited to, graphite or polypyrrolle and it thus generates an ion selective electrode which will be sensitive to the analyte (A) whose protonated form is the cation $[H_xA]^{x+}$ of the salt.

The composition of the membrane of the invention, as regards the nature of the constituents and its weight %, anion, plasticizing agent and thermoplastic material along with other elements, if appropriate, will depend on the analyte A to be measured and will vary in each case.

At the same time, the cation of A, $[H_xA]^{x+}$, may require a value that is different from x, which can be achieved through a higher or lower concentration of the acid at the time of its protonation. Thus, in order to prepare the salt [cation][anion], A is dissolved in a solution, generally aqueous, but it can be also another solvent containing a certain concentration of acid depending on the protonation level required. For example, A can have two or more nitrogen atoms in its molecule, and since it is not convenient to protonate all of them in order to obtain better selectivity of the sensor, an anion consisting of a cluster which contains boron atoms, such as, for example, but not limited to, an anion $[Co(C_2B_9H_{11})_2]^-$ or other borane, carborane or metallocarborane, is added to this solution and a precipitate, [cation][anion], is obtained. This precipitate should be filtered out and dried, and thus it will be ready to be mixed with the other components of the membrane.

Therefore, both the membrane and the ISE, as well as the sensor of the present invention, are designed from the compound to be measured, A, with nitrogen atoms in its molecule, which can be protonated or are already in a form that is positively charged. From hereon, a salt, [cation][anion], is obtained with an anion, as described in the present invention. This salt is mixed in PVC or another thermoplastic material and a plasticizing agent. The chemical composition of the membrane, the protonation level of A, and the proportion of the components are obtained through an optimization process of the sensor response to the concentration of A in a test solution, where the linearity of the physical response to the concentration is sought, which in the case of a potentiometric sensor is closest to 60 mV/z, where z is the charge of the analyte, the best sensitivity, i.e. the minimal concentration, which can be detected, and the best sensitivity to other interferential ions.

The membrane of the invention is the sensitive part of the device for measuring analytes which contain nitrogen atoms in their molecule.

Therefore, another aspect of the invention relates to the use of the potentiometric sensor of the invention or the ion selective electrode for detection and/or quantification of an analyte which contains at least one nitrogen atom.

Another aspect of the invention relates to the use of the potentiometric sensor of the invention or the ion selective electrode of the invention for selective detection and/or quantification of enantiomers.

Preferably, the detection and/or quantification take place in biological fluids (blood, plasma, serum or urine) or other liquids—natural or synthetic.

In the description and in the claims, the word "comprise" and its variants do not intend to exclude other technical characteristics, additives, components or steps. For persons skilled in the art, other objects, advantages and characteristics of the invention can be inferred in part from the description and in part from the practice of the invention. The following examples are provided as an illustration and are not intended to delimit the present invention.

EXAMPLES

The invention is illustrated here below on the basis of tests performed by the inventors which show the selectivity of the ISEs of the invention.

Example 1

ISE for Pyrazinamide

Preparation of the Ion Pair Salt:

In first place, $H^+[Co(1,2-C_2B_9H_{11})_2]^-$ was obtained from $Cs[Co(1,2-C_2B_9H_{11})_2]$ (0.30 g) and 1M HCl (15 mL), extracting the product with diethyl ether (20 mL). The extraction was repeated 3 times. The obtained solid was dried in vacuum until reaching constant weight. Pyrazinecarboxamide (PZA) (0.0123 g) was dissolved in 10 mL of 3M HCl with stirring (solution 1). In second place, the compound ion pair $H[H—PZA]_2[cos]_3$ was prepared by mixing 10 mL of 0.01M "solution 1" with 10 mL of a solution of 0.01M $H^+[Co(1,2-C_2B_9H_{11})_2]^-$ also with stirring resulting in yellow precipitate. The precipitate was filtered, rinsed with a solution of 0.1M HCl, and dried in vacuum.

Preparation of the Ion Selective Electrode:

The composition of the ISE membrane for detecting pyrazinamide was prepared by dissolving 7.0% (w/w) (0.040 g) of $H[H—PZA]_2[cos]_3$ in 63.0% (w/w) (0.360 g) of plasticizer (o-nitro phenyl octyl ether, NPOE or di-octyl phthalate, DOP or di-butyl phthalate, DBP) under stirring. Afterwards, 30.0% (w/w) of PVC (0.1714 g) powder was spread in 6 mL of THF with stirring until a viscose and clear solution was obtained. These two solutions were mixed by stirring them until homogeneity was reached. This mixture was deposited carefully with a pipette on the surface of the electrode body, and the solvent was allowed to evaporate at ambient temperature for two days. When the electrodes are not used, they are stored in air, but before use they have to be kept for 2 h in a diluted solution of analyte ($10^{-4}$M).

Equipment used:
1. Crison micropH 2000 pH/millivoltmeter
2. Ag/AgCl, KCl electrode of reference
3. The body of the ion selective electrode was prepared according to S. Alegret, et al. (S. Alegret, J. Alonso, J. Bartroli, J. M. Paulis, J. L. F. C. Lima and A. A. S. C. Machado, *Anal. Chim. Acta*, 1984, 164, 147)

As shown in tables 1 and 2, the ISEs for PZA showed good results, high selectivity and excellent proprieties of the electrode. Although the general composition of the membrane was similar, the results have indicated that the PVC membrane containing NPOE as plasticizer offered the best results with a slope of 56.98 mV/decade, linearity in the range of concentration $5.00·10^{-4}$-$1.00·10^{-1}$M, with a detection limit $3.00·10^{-5}$ M and a minimum (proven) average lifespan of 45 days.

TABLE 1

PZA characteristics of the electrode

| Plasticizer | NPOE | DOP | DBP |
|---|---|---|---|
| Slope mV/decade | 56.98 | 46.70 | 46.64 |
| Coefficient of correlation | 0.9971 | 0.9975 | 0.9988 |
| Concentration range (M) | $5.00·10^{-4}$- $1.00·10^{-1}$ | $5.00·10^{-5}$- $1.00·10^{-1}$ | $5.00·10^{-5}$- $1.00·10^{-1}$ |
| Detection limit (M) | $3.00·10^{-5}$ | $1.00·10^{-5}$ | $2.00·10^{-5}$ |
| Response time/s | <5 | <5 | <5 |
| Average lifespan/days | >45 | >45 | >45 |
| pH | 2.20-9.50 | 2.20-9.50 | 2.20-9.50 |

TABLE 2

Coefficients of selectivity of the PZA electrode for different ions

| Interference types | NPOE | DOP | DBP |
|---|---|---|---|
| $Na^+$ | −3.36 | −5.19 | −4.36 |
| $K^+$ | −5.32 | −6.39 | <−7 |
| $Ca^{2+}$ | −6.34 | <−7 | <−7 |
| $Mg^{2+}$ | −4.32 | <−7 | <−7 |
| INH | <−7 | <−7 | <−7 |
| sulfanilamide | −6.02 | <−7 | <−7 |

Table 2 shows the coefficients of selectivity for ions of biological importance along with INH (isoniazid) antibiotics and sulfanilamide. The potentiometric coefficients of selectivity ($K^{pot}_{A/B}$) were determined by using the method of fixed interference (FIM). The basic concentration was maintained constant at $10^{-3}$ M for all interference ions.

Example 2

ISE for DL-Tryptophan (DL-Try)

Preparation of the Ion Pair Salt:

In first place, $H^+[Co(1,2-C_2B_9H_{11})_2]^-$ was obtained from $Cs[Co(1,2-C_2B_9H_{11})_2]$ (0.3000 g) and 1M HCl (15 mL), extracting the product with diethyl ether (20 mL). The extraction was repeated 3 times. The obtained solid was dried in vacuum until reaching constant weight. DL-tryptophan (0.0102 g) was dissolved in 5 ml of 3M HCl with stirring (solution 1). In second place, the compound ion pair $[Try]^+[cos]^-$ was prepared by mixing the "solution 1" with 0.0165 g of $H^+[Co(1,2-C_2B_9H_{11})_2]^-$ also with stirring resulting in yellow precipitate. The precipitate was filtered, rinsed with a solution of 0.1M HCl, and dried in vacuum.

Preparation of the Ion Selective Electrode:

The composition of the membrane of ISE for detection of DL-tryptophan was prepared by dissolving 4.0% (w/w) (0.0400 g) of $[Try]^+[cos]^-$ in 63.0% (w/w) (0.6300 g) plasticizer (di-butyl phthalate, DBP) under stirring. Afterwards, 33.0% (w/w) of PVC (0.3300 g) powder was spread in 6 mL of THF with stirring until a viscose and clear solution was obtained. These two solutions were mixed by stirring them until homogeneity was reached. This mixture was deposited carefully with a pipette on the surface of the body of the electrode, and the solvent was allowed to evaporate at ambient temperature for two days. Another ISE membrane for DL-tryptophan was obtained by dissolving 7.0% (w/w) (0.0700 g) [Try]$^+$[cos]$^-$ in 31.0% (w/w) (0.3100 g) plasticizer (bis(2-ethylhexyl)phthalate) under stirring. Afterwards, 62.0% (w/w) of PVC (0.6200 g PVC) powder was spread in 2 mL THF and was treated as shown above.

When the electrodes are not used, they are stored in air, but before use they have to be kept for 2 h in a diluted solution of analyte ($10^{-4}$M).

The following equipment was used:
1. Crison micropH 2000 pH/millivoltmeter
2. Ag/AgCl, KCl electrode of reference
3. The body of the ion selective electrode was prepared according to S. Alegret, et al. (S. Alegret, J. Alonso, J. Bartroli, J. M. Paulis, J. L. F. C. Lima and A. A. S. C. Machado, *Anal. Chim. Acta*, 1984, 164, 147)

As shown in tables 3 and 4, the ISEs for DL-Try showed good results, high selectivity and excellent proprieties of the electrode. The results have indicated that the PVC membrane containing DBP as plasticizer offered the best results with a slope of 57.25 mV/decade, linearity in the range of concentration $5.00 \cdot 10^{-6} - 1.00 \cdot 10^{-1}$M, with a detection limit $1.00 \cdot 10^{-6}$ M and a minimum (proven) average lifespan of 45 days.

TABLE 3

DL-Try characteristics of the electrode

| Plasticizer | DBP | bis(2-ethylhexyl)phthalate |
|---|---|---|
| Slope mV/decade | 57.25 | 50.67 |
| Coefficient of correlation | 0.9924 | 0.9966 |
| Concentration range (M) | $5.00 \cdot 10^{-6} - 1.00 \cdot 10^{-1}$ | $5.00 \cdot 10^{-5} - 1.00 \cdot 10^{-1}$ |
| Detection limit (M) | $1.00 \cdot 10^{-6}$ | $1.00 \cdot 10^{-5}$ |
| Response time/s | <5 | <5 |
| Average lifespan/days | >45 | >45 |

TABLE 4

Selectivity coefficients of the DL-Try electrode for different amino acids.

| Type of interference | DBP | bis(2-ethylhexyl)phthalate |
|---|---|---|
| glycine | −3.66 | −2.86 |
| β-alanine | −2.11 | −2.80 |
| DL-leucine | −4.91 | −3.26 |
| DL-methionine | −4.63 | −2.73 |
| L-arginine | −4.07 | −3.48 |
| L-histidine | −3.18 | −2.61 |

Table 4 shows the selectivity coefficients for other amino acids. The potentiometric coefficients of selectivity ($K^{pot}_{A/B}$) were determined by using the method of fixed interference (FIM). The basic concentration was maintained constant at $10^{-3}$ M for all interference ions.

REFERENCES

1. Safavi, A.; Abbasitabar, F.; Hormozi Nezhad, M. R. *Chem. Anal.—Warsaw* 2007, 52, 835.
2. Shahrokhian, S.; Amiri, M.; *Microchim. Acta* 2007, 157, 149.
3. Milán-Segovia, R.; Pérez-Flores, G.; Torres-Tirado, J. D.; Hermosillo-Ramírez, X., Vigna-Pérez, M., Romano-Moreno, S. *Acta Chromatogr.* 2007, 19, 110.
4. Nemutlu, E.; Ç elebier, M.; Uyar, B.; Altinöz, S. *J. Chromatogr. B.* 2007, 854, 35.
5. Xiong, Y.; Zhou, H.; Zhang; Z.; He, D.; He, C. *Spectroc. Acta Pt. A—Molec. Biomolec. Spectr.* 2007, 66, 341.
6. Majidi, M. R.; Jouyban, A.; Asadpour-Zeynali, K. *J. Electroanal. Chem.* 2006, 589, 32.
7. Quintino, M. S. M.; Angnes, L *J. Pharm. Biomed. Anal.* 2006, 42, 400.
8. Hao, Y. X.; Xiao, Y. H. *Anal. Lett.* 2005, 38, 1405.
9. Calleja I., Blanco-Prieto M J, Ruz N, Renedo M J, Dios-Vieitez M C, *J Chromatogr A*, 2004, 1031, 289
10. D. T.-T. Nguyen, D. Guillarme, S. Rudaz, J. L. Veuthey, *J. Sep. Sci*, 2008, 31, 1050.
11. P. Scherpenisse, A. A. Bergwerff, *Anal. Chim. Acta*, 2005, 529, 173.
12. T. Goldmann, F. Taroni, P. Margot, *J. Forensic Sci.*, 2004, 49, 716.
13. L.-H. Ahlström, E. Björklund, L. Mathiasson, *Anal. Bioanal. Chem.*, 2005, 382, 1320
14. A. R. Fiorucci, E. T. G. Cavalheiro, *J. Pharm. Biomed. Anal.* 28 (2002) 909-915.
15. Y. D. Liang, J. F. Song, *J. Pharm. Biomed. Anal.*, 2005, 38, 100
16. K. D. Altria, P. Harkin, M. G. Hindson, *J. Chromatogr. Biomed.* 1996, 686, 103
17. A. M. El-Brashy, S. M. Al-Ghannam, *Microchem. J.*, 1996, 53, 420
18. Z. J. Shen, Z. M. Sun, L. Wu, K. Wu, S. Sun, Z. B. Huang, *J. Chromatogr. A*, 2002, 979, 227
19. L. Moreno, A. Merkoçi, S. Alegret, S. Hernández-Cassou, J. Saurina, *Anal. Chim. Acta*, 2004, 507, 251.
20. S. T. Sulaiman, Y. O. Hameed, *Anal. Chim. Acta*, 1988, 206, 379.
21. J. A. Tong, X. J. Dang, H. L. Li, *Electroanalysis*, 1997, 9, 165.
22. Vasjari M., Merkoçi A., Hart P. J., Alegret S., *Microchim. Acta* 2005, 150, 233.
23. M. M. Yust, J. Pedroche, J. Giròn-Calle, J. Vioque, F. Millán, *Food Chem.* 2004, 85, 317.
24. Meng Liang Wen, Yi Bin Zhao, Xiang Chen, Chang Yi Wang, *J. Pharm. Biomed. Anal.*, 1999, 18, 957.
25. G. E. Baiulescu, V. V. Cosofret, *Applications of ion selective membrane electrodes in organic analysis*, 1977, Wiley, New York.
26. T. S. Ma, S. S. M. Hassan, *Organic Analysis Using Ion-Selective Electrodes*, 1982, Academic Press, London.
27. E. G. Kulapina, O. V. Barinova, *J. Anal. Chem.*, 2001, 56, 518
28. J. Wang, Analytical Electrochemistry, 3rd Edition, Wiley-VCH, New York, 2006.
29. R. De Marco, G. Clarke and B. Pejcic, Electroanalysis, 2007, 19-20, 1987.
30. L. Campanella, F. Mazzei, R. Sbrilli, M. Tomassetti, *J. Pharm. Biomed. Anal.*, 1988, 6, 299.
31. Vladimir V. Egorov, Alexander A. Bolotin, *Talanta*, 2006, 70, 1107

The invention claimed is:
1. A membrane for a potentiometric sensor, comprising:
   a thermoplastic material,
   an electroactive substance based on a salt wherein the cation is the protonated form of the analyte to be determined and the anion is a cluster which comprises boron atoms; and
   a plasticizing agent.
2. The membrane according to claim 1, wherein the anion is mono- or polyanionic.

3. The membrane according to claim 1, wherein the boron cluster is selected from a list comprising a borane, a carborane or a metallocarborane.

4. The membrane according to claim 3, wherein the borate has the formula $(B_nH_n)^{2-}$, $(B_nX_mH_{n-m})^{2-}$ or $(LB_nH_n)^-$, wherein:
- n has a value between 6 and 12.
- X is selected from a list that comprises hydrogen (H), halogen, an alkyl group or an aryl group,
- m is a value between 0 and 12,
- L is a XR'R''R''' or XR'R'' group, where X is an N, P, S or O atom and R', R'' and R''' are radicals; equal or different, selected among, one atom of H, one alkyl group or one aryl group.

5. The membrane according to claim 3, wherein the carborane has the formula $(RCB_nH_n)^-$ or $(RCB_nX_mH_{n-m})^-$, wherein:
- R is H, an alkyl group or an aryl group,
- n has a value between 5 and 11,
- X is a halogen, an alkyl group or an aryl group, and
- m has a value between 0 and 11.

6. The membrane according to claim 3, wherein the metallocarborane has the formula $[M(C_2B_9H_{11})_2]^-$, $[M(C_2B_9H_{11})_2]^{2-}$, any of their derivatives or any mono- or di-ionic combination of at least two metallocarboranes, where M is a trivalent or divalent metal.

7. The membrane according to claim 1, wherein the thermoplastic material is polyvinylchloride (PVC).

8. The membrane according to claim 1, wherein the plasticizing agent is selected from a list comprising a polycarboxylic acid or any of its salts, benzoate, epoxydized vegetable oil, sulfonamide, organophosphate, polyether derived from glycol or any polymeric plasticizer derived from nitrobenzene.

9. The membrane according to claim 8, wherein the polycarboxylic acid is selected from a list comprising phthalic acid, adipic acid, sebacic acid or maleic acid.

10. An ion selective electrode (ISE), comprising a membrane according to claim 1 on an electrical conductor or semiconductor support.

11. The ion selective electrode according to claim 10, wherein the support is graphite, any combination with graphite or an organic polymer.

12. A potentiometric sensor, comprising an ion selective electrode according to claim 10 and a transducer.

13. A method for the detection and/or quantification of an analyte containing at least one nitrogen atom comprising using the potentiometric sensor according to claim 12 or the ion selective electrode according to claim 10.

14. A method for the selective detection and/or quantification of enantiomers comprising using the potentiometric sensor according to claim 12 or the ion selective electrode according to claim 10.

15. The method according to claim 13, wherein the detection is performed in biological fluids or other liquids—natural or synthetic.

16. The method according to claim 14, wherein the detection is performed in biological fluids or other liquids—natural or synthetic.

* * * * *